(12) United States Patent
Tang et al.

(10) Patent No.: US 8,764,947 B2
(45) Date of Patent: Jul. 1, 2014

(54) METHOD AND SYSTEM FOR DISPOSAL OF FURFURAL WASTEWATER AND METHOD AND SYSTEM FOR FURFURAL PRODUCTION

(75) Inventors: Yilin Tang, Shandong (CN); Chengzhen Jiang, Shandong (CN); Shaofeng Gao, Shandong (CN); Dongsheng LV, Shandong (CN); Zujiang Shen, Shandong (CN); Xuanwei Suo, Shandong (CN)

(73) Assignee: Jinan Shengquan Group Share-Holding Co., Ltd. (CN)

( * ) Notice: Subject to any disclaimer, the term of this patent is extended or adjusted under 35 U.S.C. 154(b) by 1104 days.

(21) Appl. No.: 12/308,153

(22) PCT Filed: Nov. 8, 2006

(86) PCT No.: PCT/CN2006/002985
§ 371 (c)(1),
(2), (4) Date: Mar. 23, 2009

(87) PCT Pub. No.: WO2007/140661
PCT Pub. Date: Dec. 13, 2007

(65) Prior Publication Data
US 2009/0194407 A1 Aug. 6, 2009

(30) Foreign Application Priority Data
Jun. 7, 2006 (CN) .......................... 2006 1 0044393

(51) Int. Cl.
*B01D 3/34* (2006.01)
*C07C 45/82* (2006.01)

(52) U.S. Cl.
USPC ................. 203/6; 203/17; 422/187; 549/489; 549/490

(58) Field of Classification Search
USPC .................. 203/6, 17; 422/187; 549/489, 490
See application file for complete search history.

(56) References Cited

U.S. PATENT DOCUMENTS

| 1,735,084 | A | * | 11/1929 | Brownlee et al. | 549/489 |
| 1,927,649 | A | * | 9/1933 | Noack | 122/31.1 |
| 1,960,812 | A | * | 5/1934 | Blomqvist et al. | 549/489 |

(Continued)

FOREIGN PATENT DOCUMENTS

| CN | 1327953 | 12/2001 |
| CN | 1629151 | 6/2005 |
| WO | WO-03/091163 A2 | 11/2003 |

OTHER PUBLICATIONS

"International Patent Application Serial No. PCT/CN2006/002985, International Search Report mailed Mar. 22, 2007", 6 pgs.

*Primary Examiner* — Robert A Hopkins
(74) *Attorney, Agent, or Firm* — Schwegman Lundberg & Woessner, P.A.

(57) ABSTRACT

A method and system for disposal of furfural wastewater, wherein raw crop material is transported into a hydrolysis reactor after crushed and mixed with acid to be hydrolyzed to form raw furfural liquid, and then said raw furfural liquid is transported into a distillation column to be distilled, during which furfural wastewater is discharged from said distillation column. Firstly said furfural wastewater is transported into a wastewater evaporation system to be heated it into wastewater vapor which is then transported back into said hydrolysis reactor to form recycle of said furfural wastewater. Wastewater vapor residues generated therein can be utilized directly to combust in boiler, mix with acid, or prepare end product acetate. The system for disposal of furfural wastewater comprises at least a wastewater evaporation system connecting with a heat resource which is one of steam, electricity, coal, oil, gas, plant straws or wastewater vapor residues. The present invention further provides a method and system for furfural production utilizing said method and system for disposing the wastewater. The present invention realizes furfural production with no pollution.

17 Claims, 5 Drawing Sheets

(56) References Cited

U.S. PATENT DOCUMENTS

| | | | |
|---|---|---|---|
| 2,409,781 A * | 10/1946 | Mertz | 203/7 |
| 3,470,853 A * | 10/1969 | Knizia | 122/406.4 |
| 4,066,691 A * | 1/1978 | Schroeder | 562/537 |
| 4,164,848 A * | 8/1979 | Gilli et al. | 60/652 |
| 4,357,214 A | 11/1982 | La Mori et al. | |
| 4,366,322 A * | 12/1982 | Raymond | 549/489 |
| 4,533,743 A * | 8/1985 | Medeiros et al. | 549/489 |
| 4,912,237 A * | 3/1990 | Zeitsch | 549/489 |

* cited by examiner

METHOD AND SYSTEM FOR DISPOSAL OF FURFURAL WASTEWATER AND METHOD AND SYSTEM FOR FURFURAL PRODUCTION

TECHNICAL FIELD OF THE INVENTION

This invention relates to a method and system for the disposal of furfural wastewater, and a method and system for furfural production utilizing said method and system for disposing the wastewater.

BACKGROUND OF THE INVENTION

Most of furfural production processes utilize direct method, wherein the catalyst is sulfuric acid, and the majority of the raw materials use corn-cob, some of them use other agriculture residues such as corn stalk, cotton stalk, cotton shell, bagasse and etc. Usually, the raw material is crushed down by a crusher(s) and then added dilute sulfuric acid and stirred by an acid mixer(s) until uniformly mixed. The mixture is transported into a hydrolysis reactor. In the reactor, steam is transported into from the bottom and the hydrolyzed furfural is carried out together with the rising steam to form hydrolyzed furfural vapor. The hydrolyzed furfural vapor is transformed into raw furfural liquor after cooling, which is transported into the distillation column to be distilled. Azeotrope of furfural and water is distilled out from the top of the column. After phase separating, the azeotrope is separated into furfural phase which is named as raw furfural, and water phase which flows back into the column. The wastewater discharged from the bottom of the column which includes water, acetic acid and high boiling residues formed during the hydrolysis process, is the furfural wastewater, or called as column bottom furfural wastewater. The raw furfural is then transported into a refining system after further neutralized to be refined into end product furfural. Wastewater including water and a small quantity of furfural is generated during the refining process.

The main components of the column bottom furfural wastewater which is generated during the furfural production process are acetic acid, organic high boiling residues, a small quantity of furfural, and hydrophobic oil-fat substances. Its PH value ranges from 2 to 3 with COD (Chemical Oxygen Demand) as high as from 16,000 to 20,000 generally. The main components of the wastewater generated during the refining process are water and a small quantity of furfural, wherein the COD is usually above 20,000. Nowadays, the disposal of furfural wastewater has been restricting the development of furfural production because of its high COD and the large quantities of wastewater. Small scale furfural manufactures are not available to establish wastewater disposal facilities. They will not be able to dispose the wastewater completely because of the high cost of wastewater disposal even if they invest and construct the wastewater disposal facilities. While large scale furfural manufactures have to increase the cost of furfural production also because of the relatively high wastewater disposal cost. So many developed countries have turned to simply buy the end product furfural from developing countries instead of manufacturing in their own countries as the wastewater is hard to be disposed. The biological contact oxidation method is mostly utilized to dispose the furfural wastewater in China, wherein the wastewater is neutralized, flocculated and sedimentated with lime milk firstly, and then disposed by anaerobic-aerobic method. There are some knotty problems with this method as follows:

1. The calcium salts dissolved in the water after neutralized by lime milk scale on the surfaces of elastic fillers in the anaerobic pool as temperature promoting so as to reduce the adhesion quantities of anaerobic sludges on the surfaces of the elastic fillers, which gradually deteriorates the effect of the anaerobic disposal. If the sodium carbonate or the sodium hydroxide is used for neutralization instead, the cost of disposal will increase sharply.

2. Unlike the wastewater in liquor industry containing large quantities of nutrients such as carbohydrates, the wastewater herein just has few nutrients for anaerobic bacteria together with that the sludge gradually reduces with the wastewater draining during the wastewater disposal process, so, the sludge should be supplied into the wastewater during the process according to this method.

Since it is under certain temperatures that the anaerobic bacteria has better abilities to dispose organics, this method is not suitable in northeast China where the furfural raw materials are abundant but the climate is very cold. This is one of the reasons why the furfural industry is stagnant in northeast China.

This method requires large investment, large area occupation, high running expense, and usually needs 2-3 steps of anaerobic disposal to completely reach the discharge standard.

Additionally, patent application No. 200410011121.2 disclosed a method that after evaporated with furfural vapor, concentrated and then added with dilute acid, the wastewater was utilized to be mixed with acid. But this method has problems shown below:

There are a large quantity of acetic acid and a small quantity of furfural in the wastewater which form secondary pollution during the wastewater evaporation process, since the acetic acid and furfural thereof can not be recycled.

In summary, there exists serious pollution in traditional technologies for discharging of furfural wastewater. It will cause extreme damages to the environment if the problem is not solved.

SUMMARY OF THE INVENTION

The first aim of the present invention is to provide a method for furfural wastewater disposal with nearly no pollution.

The second aim of the present invention is to provide a system for furfural wastewater disposal with nearly no pollution.

The third aim of the present invention is to provide a method of furfural production with nearly no pollution.

The forth aim of the present invention is to provide a system of furfural production with nearly no pollution.

For achieving the first aim, techniques of the present invention are as follows:

1. A method for disposal of furfural wastewater, wherein raw crop material is transported into a hydrolysis reactor after crushed and mixed with acid to be hydrolyzed to form raw furfural liquid, and then said raw furfural liquid is transported into a distillation column to be distilled, during which furfural wastewater is discharged from said distillation column, wherein said method comprising:
(a). transporting said furfural wastewater into a wastewater evaporation system and then heating it into wastewater vapor;
(b). transporting said wastewater vapor back into said hydrolysis reactor to form recycle of said furfural wastewater.

2. The method further comprises cushioning said furfural wastewater to regulate the balance between wastewater vaporing and wastewater inputting before transporting said furfural wastewater into said wastewater evaporation system.

3. The method further comprises sedimentating said furfural wastewater after it is discharged from said distillation column.

4. The method further comprises generating wastewater vapor residues in said wastewater evaporation system and then discharging said wastewater vapor residues.

5. The method further comprises neutralizing said furfural wastewater by adding alkali compounds before step (a), wherein said wastewater vapor residues contains acetate solution.

6. The said alkali compounds include $NaOH_2Ca(OH)_2$ and $Na_2CO_3$.

7. The said heating in step (a) is realized by utilizing steam, electricity, coal, oil, gas, plant straws or said wastewater vapor residues.

8. The said heating in step (a) is realized by utilizing steam, wherein after heat exchange with said furfural wastewater, said steam for heating is separated into separated steam and separated condensed water, then said separated steam is supplied to a steam user(s), said separated condensed water is depressurized and expanded into low pressure steam which is supplied to a steam user(s) and superheated condensed water which is directly pumped into a boiler(s) by a soft water pump so as to realize recycle of soft water.

9. The pressure of said wastewater vapor is higher than reaction pressure of said hydrolysis reactor, and pressure difference between the two ranges from 0.01 MPa to 1 MPa.

10. The pressure of said steam is higher than pressure of said wastewater vapor, and pressure difference between the two ranges from 0.01 MPa to 1 MPa. For achieving the second aim, techniques of the present invention are as follows:

11. A system for disposal of furfural wastewater for disposing wastewater of a furfural production system, wherein said furfural production system at least comprising:
a hydrolysis reactor for disposing raw crop material which is already crushed and mixed with acid, and
a distillation column, connecting with said hydrolysis reactor, said distillation column discharging said furfural wastewater, wherein said system for disposal of furfural wastewater at least comprises a wastewater evaporation system, for heating said furfural wastewater discharged from said distillation column and generating wastewater vapor, and said wastewater evaporation system connecting with said hydrolysis reactor by a wastewater vapor pipeline(s).

12. The system at least comprises a wastewater buffer vessel connecting with said wastewater evaporation system, said furfural wastewater being transported into said wastewater evaporation system via said wastewater buffer vessel which is equipped with device for regulating the balance between said wastewater vapor generated from said wastewater evaporation system and the inputting wastewater thereinto.

13. Wherein said wastewater evaporation system at least comprises a wastewater evaporator, connecting with a heat resource.

14. Wherein said wastewater evaporation system at least comprises a wastewater evaporator, connecting with said wastewater buffer vessel.

15. Wherein said distillation column is connecting with at least one wastewater sediment bowl thereafter.

16. Wherein said wastewater evaporation system comprises outlet for discharging wastewater vapor residues.

17. Wherein said heat resource comprises a vapor heating system which comprises:
a boiler, connecting with said wastewater evaporator, for generating steam used for heating which is transported into said wastewater evaporator, said furfural wastewater and said steam used for heating run respectively via different pipelines inside said wastewater evaporator and said furfural wastewater is heated by means of heat exchange;
a steam-water separator, connecting with said wastewater evaporator, wherein said steam used for heating after heat exchange in said wastewater evaporator is transported into said steam-water separator to be separated into steam and condensed water;
a steam buffer vessel, connecting with said steam-water separator, said steam generated in said steam-water separator is transported into said steam buffer vessel to be cushioned and then supplied to a steam user(s);
a steam expansion slot, connecting with said steam-water separator and said steam buffer vessel, wherein the condensed water generated in both said steam-water separator and said steam buffer vessel is transported into said steam expansion slot to be depressurized and expended for generating low pressure steam which is supplied to a steam user(s), and also for generating condensed water which is directly transported into said boiler to realize recycle of soft water.

18. Wherein said heat resource is any one or any combination on utilization of electricity, coal, oil, gas, plant straws or said wastewater vapor residues.

For achieving the third aim, techniques of the present invention are as follows:

19. A method for furfural production, wherein raw crop material is transported into a hydrolysis reactor after crushed and mixed with dilute sulfuric acid to be hydrolyzed to form raw furfural liquid, and then said raw furfural liquid is transported into a distillation column to be distilled, azeotrope of furfural and water is distilled out from the top of said distillation column and transformed into raw furfural after cooling, and said raw furfural is transported into refining system to be refined into end product furfural, while furfural wastewater is discharged from bottom of said distillation column, said method comprising one of said methods for disposal of furfural wastewater according to one of the abovementioned technique 1-technique 10.

20. Wherein the wastewater vapor residues formed after said furfural wastewater is heated into wastewater vapor are harmlessly disposed via one of three methods as follows:
(1) utilized as fuels of boiler directly;
(2) utilized as hydrolysis mixed acid in furfural production in the form of concentrated liquid;
(3) said furfural wastewater is neutralized with adding alkali compounds before step (a) in order to generate vapor residues including acetate solution.

For achieving the forth aim, techniques of the present invention are as follows:

21. A system for furfural production at least comprises:
a hydrolysis reactor for disposing raw crop material which is crushed and mixed with acid;
a distillation column connecting with said hydrolysis reactor; and
a refining system connecting with said distillation column, from the bottom of which furfural wastewater is discharged, wherein said system further comprises one of said systems for disposal of furfural wastewater listed in technique 11-technique 18.

Obviously, among the above 21 techniques, techniques 1, 11, 19, 21 are cores of the present invention from a same inventive concept, while the others can be regarded as relating detailed embodiments.

The present invention resolves the knotty problems on wastewater discharging standards and its secondary pollution via wastewater recycling during the furfural production process, not only realizing no discharge of furfural wastewater but also reducing furfural production cost greatly. The present invention is suitable for any furfural manufacturer with small investment of equipments, low cost of operation, convenient cleaning and maintenance, no negative effect on furfural yield.

The present invention has advantages and positive effects over traditional technology in the following four aspects:

1. The present invention has small area occupation and small investment in equipments. The facility can be installed as just occupying a corner of the traditional furfural workshop, solving the problems that large area occupation of the facilities such as sediment bowls, anaerobic pools, and aerobic pools according to the biological contact oxidation method. The investments on factory workshops and equipments of the present invention are much lower than that of the biological contact oxidation method.

2. The present invention has simple process, easy operation, and needs just a few operators. The present invention boasts simple process, wherein the liquid level is controlled completely by the automatic instrumentations, so there is just a need for timing inspection by the operators in the hydrolysis section instead of appointing individual special operator(s) for each of the whole production process in the traditional technology due to its very complicated design which is have to be staffed by at least 6-10 operators for monitoring and controlling all the time.

3. The present invention realizes null-discharge of the furfural wastewater, no secondary pollution so as to save a lot of cost. The present invention can not only realize the recycle of wastewater and steam during the furfural production process with no secondary pollution during the recycle process but also utilize the combustible substances in the wastewater such as acetic acid and fat since there exist a large quantity of acetic acid and a small quantity of furfural contained in the wastewater vapor residues are helpful for hydrolysis of raw materials and recovery of the furfural in the wastewater. In such way, the complete utilization and recycle for the waste disposal are realized in the present invention. Meanwhile a great deal of soft water production cost is saved by closed circulation of the steam and soft water in the present invention. In the traditional technology, the furfural wastewater can not be utilized synthetically, for some of the circumstances even if the discharged standard is achieved, it will have to consume clean water or induce secondary pollution while the pollution charge cost will have to be paid to the environment protection department.

4. The present invention boasts low operation cost, simple maintenance and low-cost for the equipments. If the steam heating method in one of the embodiments of the present invention is utilized, it will greatly reduce the operation cost due to that just a little quantity of steam and electricity is consumed at runtime because of the comprehensive utilization of the steam in comparison with the biological contact oxidation method. Moreover, the maintenance cost for the system in this embodiment is reduced because of small quantities of equipments and the simple design thereof.

The each label in the drawings stands for:

1. wastewater sediment bowl
2. wastewater pump
3. wastewater evaporator
4. wastewater buffer vessel
5. boiler
6. steam-water separator
7. steam buffer vessel
8. steam expansion slot
9. soft water pump
10. electric heating furnace
11. furnaces of coal, oil or gas

DETAILED DESCRIPTION OF THE INVENTION

The present invention has been described further combined with drawings and particular embodiments. But it should be announced that the disclosed embodiments are just used to explain the system and method of present invention, and do not limit the scope of present invention.

Figure 1:
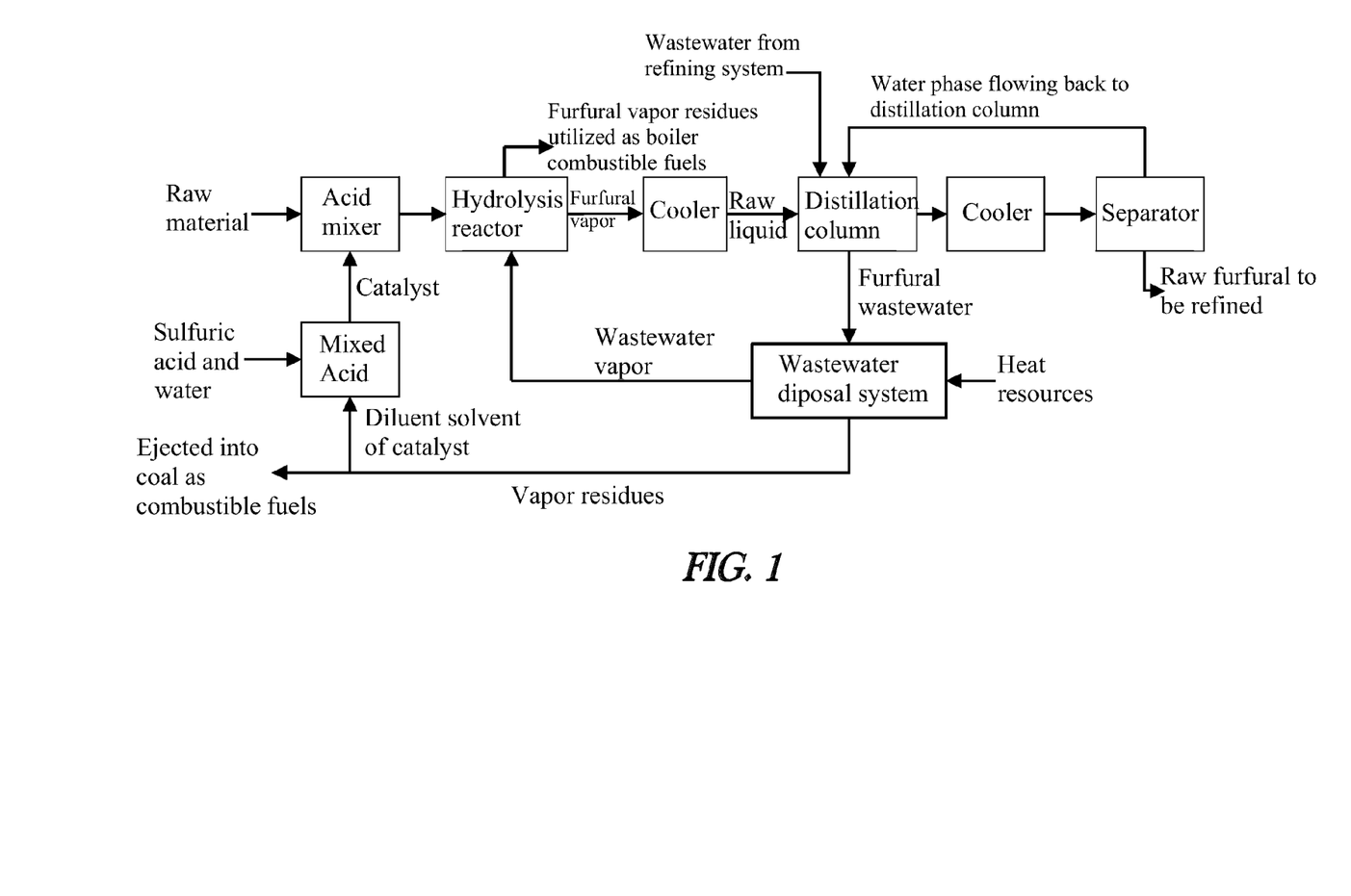
FIG. 1 is a schematic diagram showing the disposal method and system of furfural wastewater according to the present invention.

FIG. 1 is a schematic diagram showing the disposal method and system of furfural wastewater according to the present invention. It should be pointed out that the innovation of the present invention is that a wastewater disposal system is added on the basis of traditional technology, wherein the furfural wastewater discharged out from distillation column of the traditional technology is heated by a heat source(s) to transform the furfural wastewater into two products, namely wastewater vapor and vapor residues.

The wastewater vapor is then recovered by being transported in a hydrolysis reactor, which is equipped in the traditional technology, to participate in the furfural production process continuously, wherein acetic acid contained in the wastewater vapor is utilized as hydrolysis catalyst after transported into the hydrolysis reactor. This part of acetic acid is benefit for hydrolyzing plant straws such as the corn-cob, as it can increase the yield of furfural and decrease the adding quantity of hydrolysis catalyst for hydrolyzing the plant straws so as to correspondingly reduce the harmful components in the furfural residues.

The vapor residues in the present invention can also be recycled, wherein the first way is to directly eject the vapor residues into coal as combustible substances as the acetic acid therein (content is 2-4%) benefits for fuels combusting; the second way is to mix the vapor residues with dilute sulfuric acid in the form of concentrated liquid; and the third way is to neutralize the furfural wastewater by alkaline substances such as soda before transporting it into the evaporator, wherein the vapor residues discharged from the evaporation system after the evaporating process contain a large quantity of sodium acetate, solution of which can be prepared to end product sodium acetate after processes such as filtration, discoloration, evaporation/concentration, crystallization and etc.

The above is the essential principle of the present invention. Hereinafter is the detailed description.

FIG. 1 shows that furfural production process in the present invention utilizes direct method, wherein the catalyst is sulfuric acid, and majority of the raw material uses corn-cob, some of the raw material uses other agriculture residues such as corn stalk, cotton stalk, cotton shell, bagasse and etc. Usually, the raw material is crushed down by a crusher(s) and then added with dilute sulfuric acid, and stirred by an acid mixer(s) until uniformly mixed. The mixture is transported into the hydrolysis reactor. In the reactor, steam is transported into from the bottom and hydrolyzed furfural is carried out together with the rising steam to form furfural vapor which is then transformed into raw furfural liquor after cooling in a cooler, which is accordingly transported into a distillation column to be distilled. Azeotrope of furfural and water is distilled out from the top of the column. After phase separating, the azeotrope is separated into furfural phase which is named as raw furfural and water phase which flows back into the column. The raw furfural is then transported into refining system after further neutralized to be refined into end product furfural. Wastewater including water and a small quantity of furfural is also generated during the refining process. Wastewater including water, acetic acid discharged from the bottom of the column and high boiling residues formed during the hydrolysis process is the furfural wastewater, or called as column bottom furfural wastewater. The aim of the present invention is to dispose the abovementioned furfural wastewater with nearly no pollution. Firstly, as shown in FIG. 2-FIG. 5, functions and operation data of each of the equipments are explained as follows:

Wastewater sediment bowl 1: connecting with a distillation column (not shown in the figure). The furfural wastewater discharged from the distillation column is drained into wastewater sediment bowl 1, where suspended substances and sediments in the furfural wastewater are removed so as to avoid block in pipelines during distillation process. Soda can be added into wastewater sediment bowl 1 to neutralize the acetic acid if there is a need of producing sodium acetate during following processes. Wastewater sediment bowl 1 can be disposed plural levels of sediment bowls to promote sediment effect. The suspended substances and the sediments taking out of the sediment bowl 1 can be transported into a boiler as combustible fuels.

Wastewater pump 2: connecting with wastewater sediment bowl 1, which continuously pumps the sedimentated furfural wastewater into a wastewater evaporation system. The outlet pressure of wastewater pump 2 should be higher than the wastewater vapor pressure generated in the evaporation system to ensure the wastewater running under normal processes.

Wastewater evaporation system: are the core equipments of the present invention, comprising a wastewater evaporator 3 and a wastewater buffer vessel 4. The furfural wastewater is pumped into wastewater buffer vessel 4 via wastewater pump 2. The bottom of wastewater buffer vessel 4 is connected with the bottom of wastewater evaporator 3. Meanwhile hot steam generated in boiler 5 is introduced into wastewater evaporator 3, in which the furfural wastewater and the hot steam used for heating run inside different pipelines in order that the furfural wastewater is heated through heat exchange into wastewater vapor which contains relative quantities of furfural. The wastewater vapor is then transported into wastewater buffer vessel 4. After being cushioned in wastewater buffer vessel 4, the wastewater vapor is transported back into the hydrolysis reactor through a top wastewater vapor pipeline to realize recycle of the furfural wastewater. Since the bottom of wastewater evaporator 3 is connected with the bottom of wastewater buffer vessel 4 via a pipeline(s), the liquid phase generated in the cushion process can be returned to the bottom of wastewater evaporator 3 and then be heated again. In such way, thermosiphon is formed on the heated furfural wastewater between wastewater buffer vessel 4 and wastewater evaporator 3, wherein the pressure of wastewater vapor generated during the cycling process is from 0.3 to 3.0 MPa. Furthermore, an outlet for discharging vapor residues is disposed at the bottom of wastewater evaporator 3 in order to periodically discharge the vapor residues which will be further disposed.

It is necessary to regulate the liquid level in wastewater buffer vessel 4 during the cycling process, wherein the liquid level should be maintained adjacent to upper tube sheet of wastewater evaporator 3 in order to maximize the heat exchange area. In a preferred embodiment, the regulation is realized by means of controlling the outlet flow of wastewater pump 2 via a regulation valve disposed at the outlet of pump 2. The main aim of controlling the outlet flow is to basically keep a constant liquid level inside evaporator 3 to ensure the reliable running of the evaporation system by means of maintaining a basic equal quantity on the wastewater evaporated out of wastewater evaporator 3 and the wastewater pumped into wastewater buffer vessel 4 by wastewater pump 2. In such a process, the liquid level in wastewater buffer vessel 4 is also regulated. Commonly the pressure of the steam here is higher than the wastewater vapor pressure of wastewater evaporation system. The preferred pressure difference between the two should be above 0.01 MPa, best of which is between 0.01 MPa-1 MPa. The steam can be the saturated steam or the superheated steam under corresponding pressures.

The wastewater vapor pressure in the wastewater evaporation system is commonly higher than reaction pressure of the hydrolysis reactor. In one of the embodiments of the present invention the reaction pressure of the hydrolysis reactor is from 0.1 MPa to 3 MPa, while the wastewater vapor pressure in the wastewater evaporation system is usually at least 0.01 MPa higher than the reaction pressure of the hydrolysis reactor. The preferred pressure difference between the two ranges from 0.01 Mpa to 1 Mpa.

In the present invention, the wastewater vapor pressure should be higher than reaction pressure of the hydrolysis reactor to ensure the wastewater vapor to be transported into the hydrolysis reactor continuously as heat source and to carry the hydrolyzed furfural out of the hydrolysis reactor. Otherwise, substances in the hydrolysis reactor will be pushed back into the wastewater vapor pipeline and block the pipeline if the reaction pressure of hydrolysis reactor is higher than the wastewater vapor pressure. Steam pressure must be higher than the wastewater vapor pressure. As for saturated steam, high pressure causes high temperature, so the steam temperature must be higher than the wastewater vapor temperature to ensure the wastewater vapor to be heated and vapored continuously. The steam pressure cannot be lower than the wastewater vapor pressure as long as the wastewater is heated and vapored.

Figure 2:
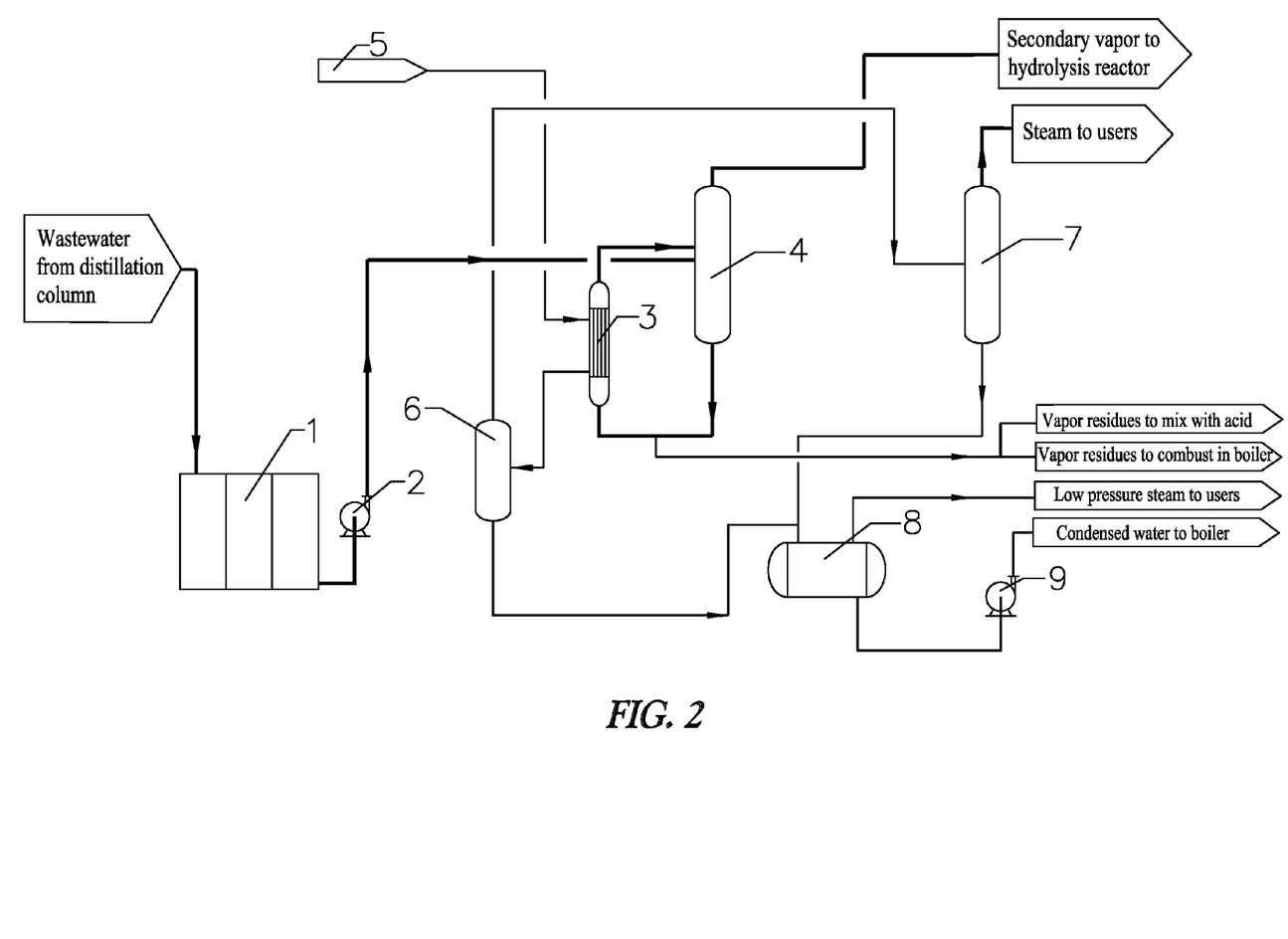
FIG. 2 is a schematic diagram according to an embodiment of the present invention, wherein the vapor residues are used for mixing with acid or as boiler combustible material.
Figure 3:
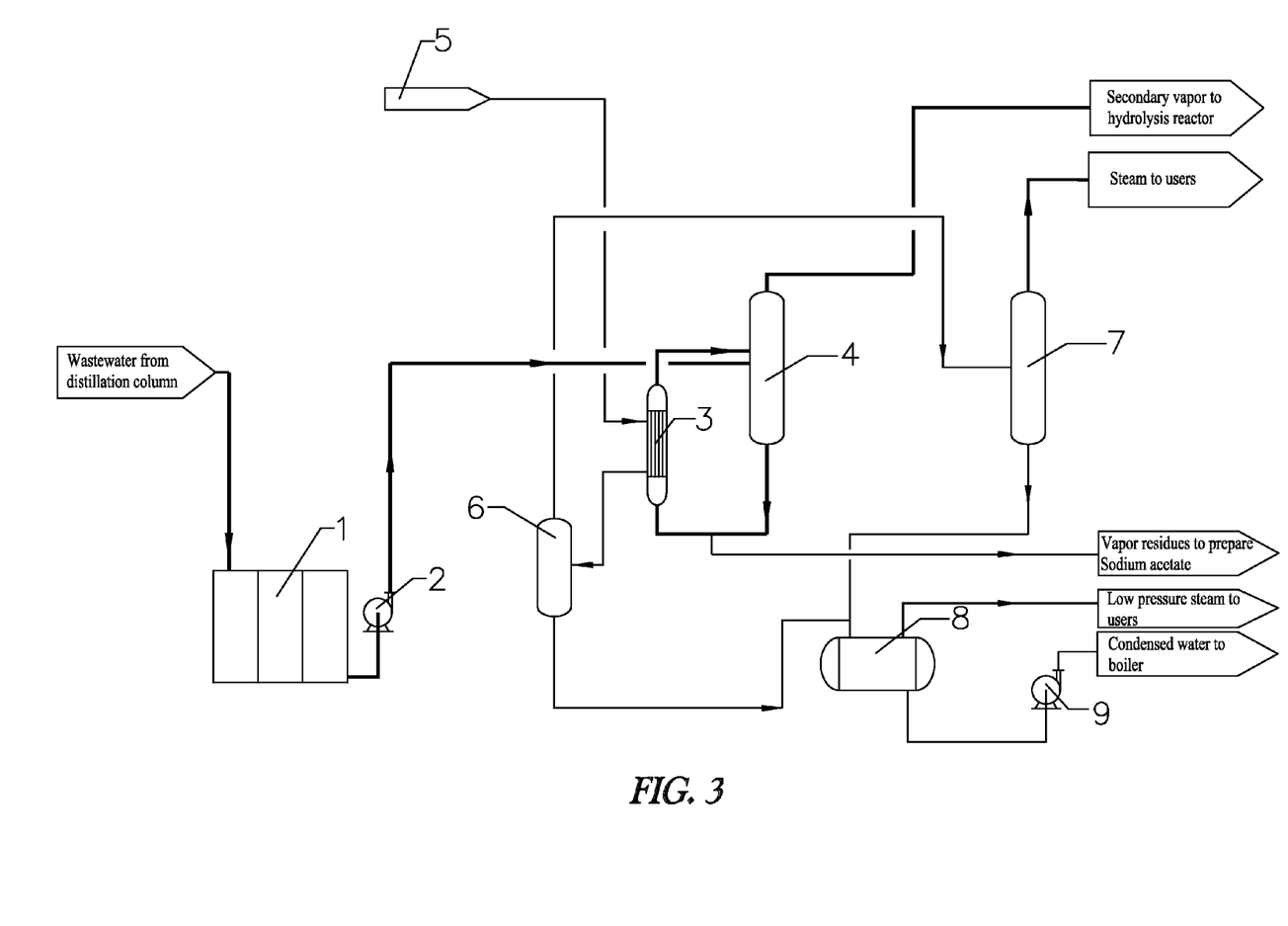
FIG. 3 is a schematic diagram of according to an embodiment the present invention, wherein the vapor residues are used to produce sodium acetate after the wastewater is neutralized.

Steam-water separator 6: The condensed water, which is generated after the steam from boiler 5 heats the wastewater via heat exchange in wastewater evaporator 3, is transported into steam-water separator 6 for steam-water separation, where liquid level of The condensed water is kept about 40% height in steam-water separator 6 for forming a liquid seal. The liquid level is controlled by an outlet regulation valve. The saturated steam generated after separation is transported to a steam user(s) with a pressure range from 0.3 MPa to 3.0 MPa.

Steam buffer vessel 7: The steam (pressure 0.3-3.0 MPa) generated in steam-water separator 6 is transported into steam buffer vessel 7 before supplied to a steam user(s).

Steam expansion slot 8: High pressure condensed water generated in steam-water separator 6 and condensed water generated in steam buffer vessel 7 are transported into steam expansion slot 8 to be depressurized and expanded into two products—low pressure steam and superheated condensed water, wherein the low pressure steam with 0.3-0.5 MPa pressure is supplied to other steam user(s), and the superheated condensed water is directly pumped into a boiler by soft water pump 9 to realize the recycle of soft water.

All of boiler 5, steam-water separator 6, steam buffer vessel 7, steam expansion slot 8 and soft water pump 9 hereinabove are needed only for an embodiment(s) of the system and method of the present invention wherein steam is utilized as heat resource and for steam cycling. For the other embodiment(s) wherein electricity, oil and/or gas are utilized for heating furfural wastewater instead of steam, the details are described hereinafter.

Figure 4:
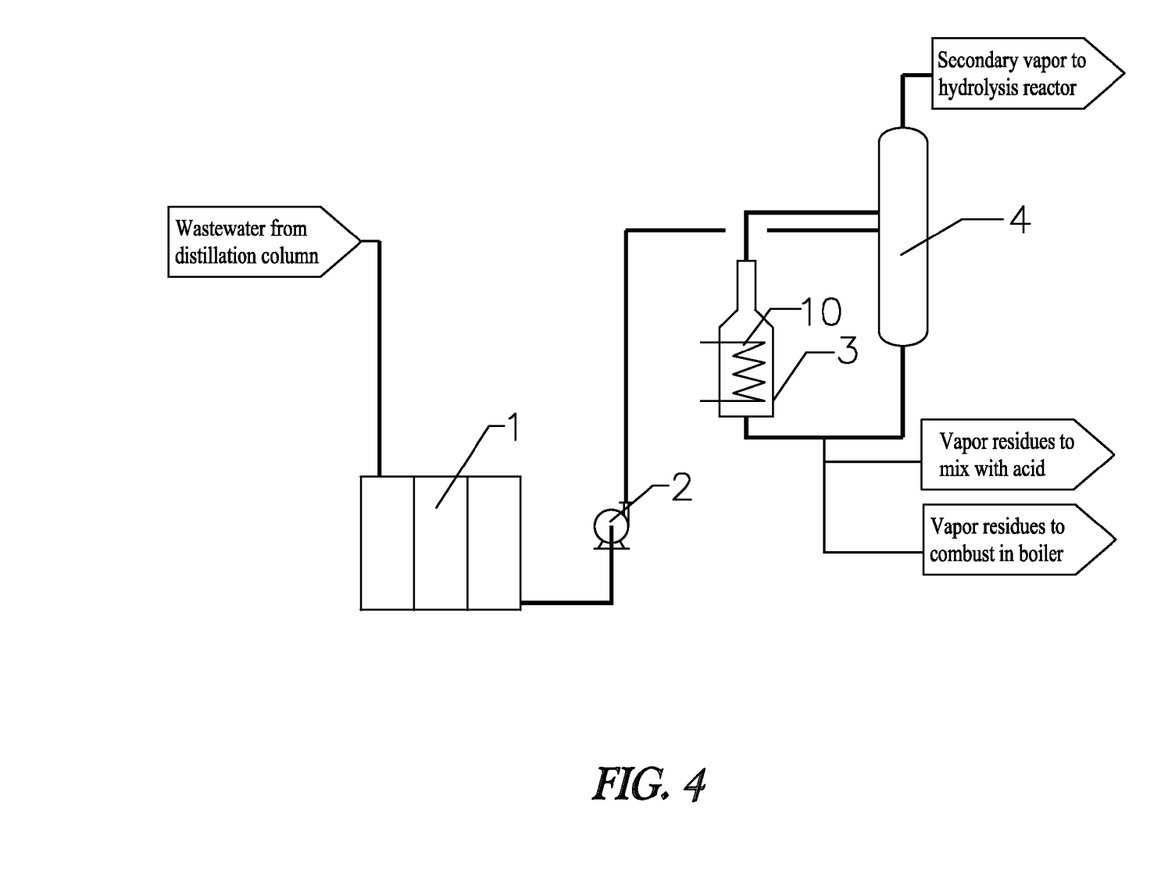
FIG. 4 is a schematic diagram according to an embodiment of the present invention, wherein the electric heating furnace is used to vaporize the wastewater.

Electric/electromagnetic heating furnace 10: In the embodiment as shown in FIG. 4, an electric/electromagnetic heating furnace 10 is utilized to heat the furfural wastewater into wastewater vapor.

Figure 5:
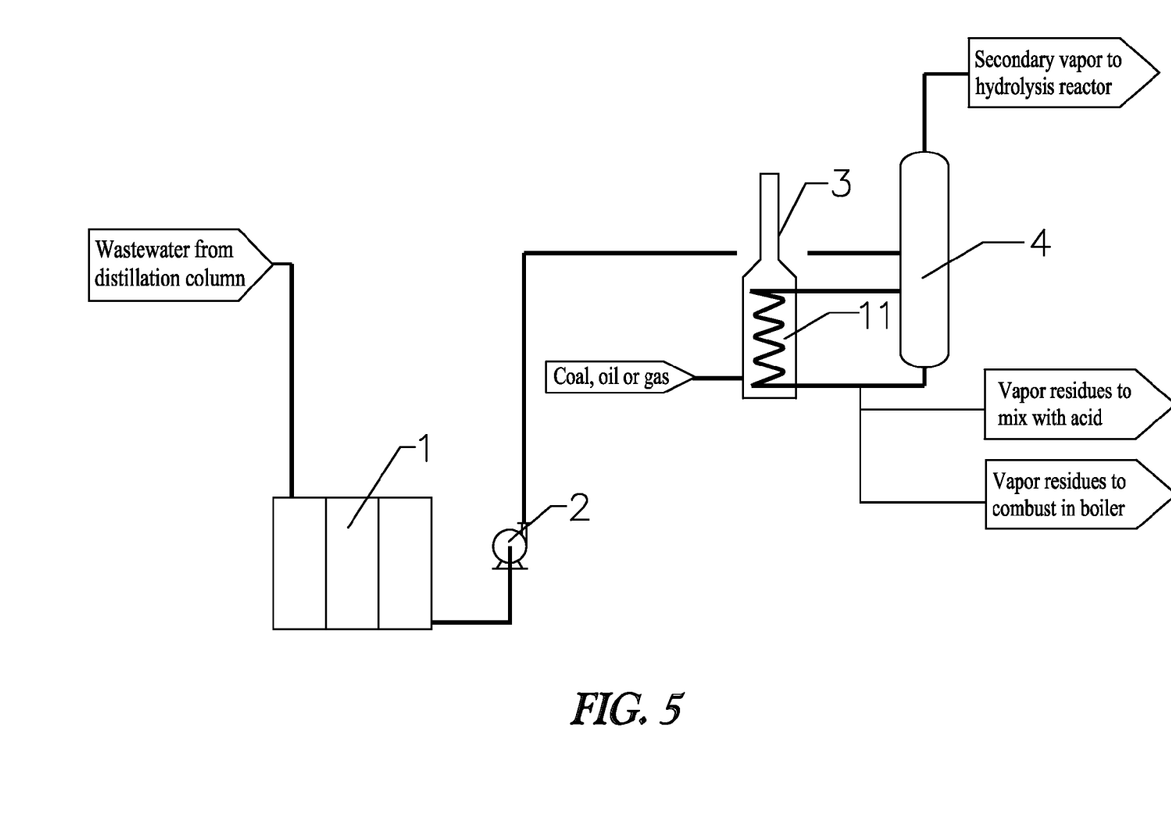
FIG. 5 is a schematic diagram according to an embodiment of the present invention, wherein furnaces of coal, oil or gas are used to vaporize the wastewater.

Furnaces of coal, oil or gas 11: In the embodiment as shown in FIG. 5, furnaces of coal, oil or gas 11 can be utilized to heat the furfural wastewater into wastewater vapor.

Furthermore, other heat sources can also be utilized in the present invention, such as electricity, coal, oil, gas and even plant straw or its residues, or any combination of any heat source said above.

Steps of abovementioned process are concluded hereinafter:

Firstly, furfural wastewater is sedimentated in wastewater sediment bowl 1 and then pumped via wastewater pump 2 into the wastewater evaporation system which comprises wastewater evaporator 3 and wastewater buffer vessel 4 in order to be heated. The wastewater vapor containing furfural generated therein is transported back into the hydrolysis reactor to participate the normal furfural production process. While the residual liquid furfural wastewater is circulated inside the wastewater evaporation system continuously. The vapor residues are periodically discharged from the bottom of wastewater evaporator 3 to be disposed further. The sedimentated and suspended substances which are generated in wastewater sediment bowl 1 are transported into boiler as combustible fuel.

Certainly, the wastewater evaporation system can also adopt other forms, such as only heating wastewater evaporator 3, or only heating wastewater buffer vessel 4, or other equipments for heating, as long as the equipment can reach the harmless disposal aim to heat and vapor wastewater.

During the process hereinabove, heating methods on furfural wastewater are listed below:

1. Heat exchange between steam and furfural wastewater for heating the wastewater into wastewater vapor;
2. Electric or electromagnetic heating furnace for heating the wastewater into wastewater vapor;
3. Coal burning furnace for heating the wastewater into wastewater vapor;
4. Oil or gas burning furnace for heating the wastewater into wastewater vapor.

Three methods utilized for disposal of vapor residues are listed below:

1) The residues generated in the wastewater evaporation system during the evaporation process are discharged from the bottom of the wastewater evaporation system. The generated residues are ejected into coal and combusted directly before neutralization of the furfural wastewater, which contain acetic acid (content is 2-4%) that benefits fuels combusting and enhances heat value of furfural residues.

2) The residues are mixed with acid—to prepare dilute sulfuric acid—in the form of condensed liquid; namely the residues return to the original furfural hydrolysis process as diluent solvent of furfural hydrolysis catalyst, which is utilized for mixing with dilute sulfuric acid, and the mixed dilute sulfuric acid is used for soaking raw materials such as corncob. This method causes no pollution.

The said two methods above are shown in FIG. 2.

3) As shown in FIG. 3, the furfural wastewater is neutralized by alkali compounds such as $NaOH_2Ca(OH)_2Na_2CO_3$ in wastewater sediment bowl 1 before transported into the evaporation system in order that the vapor residues discharged from evaporation system after the above processes contain a large quantity of acetate products. The solution of the acetate products is made into end acetate product after processes such as filtration, discoloration, evaporation/condensation, crystallization and etc.

Utilizing neutralization method can lower the quality grade of equipment materials of the present invention, wherein common stainless steel such as ZG0Cr18Ni9Ti, ZG0Cr18Ni9, or common carbon steel can be utilized instead of stainless steel, titanium, titanium alloy, zirconium, zirconium alloy, or other anti-corrosive metals in the traditional technology.

Moreover, the wastewater generated during the furfural refining process of traditional technology also contains a small quantity of furfural. This part of wastewater can be transported into primary furfural distillation column to be further extracted for furfural, wherein column bottom wastewater discharged from the bottom of primary distillation column can also be transported into the wastewater evaporation system to be disposed according to the present invention.

Furthermore, furfural residues in the hydrolysis reactor can also be utilized as boiler fuels, since they can reduce the harmful components in the smoke generated during the combusting process and lower the process cost. Some embodiments with further detail description are listed below showing comparison between the present invention and traditional technology on furfural production method and wastewater disposal method.

EMBODIMENT OF TRADITIONAL TECHNOLOGY

The raw material utilizes air-dried corn-cobs, which is cleaned and crushed into corn-cob granules in 1-1.5 cm particle size. The corn-cob granules are then transported into an acid mixer(s) to be mixed with acid, wherein the concentration and dosage of the acid is based on demands of traditional furfural production process. The corn-cob granules are transported into double hydrolysis reactors in series by a belt conveyer after mixed with acid. After the double hydrolysis reactors are full, steam with 1.3-1.6 MPa pressure is introduced, wherein the hydrolysis temperature is from 192° C. to 201° C., and hydrolysis time is from 0.5 to 1.2 hours. The raw hydrolyzed furfural liquid is introduced into following processes such as extracting and refining until end product furfural is obtained. The column bottom furfural wastewater is transported via a wastewater pipeline(s) to a sewage station to be disposed by means of biological contact oxidation method, wherein firstly the wastewater is neutralized by adding lime and then flocculated and sedimentated in a water sediment bowl, secondly the clear liquor in the upper part of the wastewater is transported into a two-staged anaerobic column to be disposed in series with a residence time of above 48 hours therein, and thirdly it is transported into an aerobic aeration pool for aerobic disposal and finally discharged after simple disposal. In this embodiment, it will generate 12 m³ furfural wastewater with COD from 16,000 to 18,500 for per ton furfural, while the sewage quantity after disposed is 14 m³ with COD from 110 to 130. The furfural yield of this embodiment is 9-10%, and the detailed technical index is shown in Table 1.

Embodiment 1 of the Present Invention

The raw material utilizes air-dried corn-cobs, which is cleaned and crushed into corn-cob granules in 1-1.5 cm particle size. The corn-cob granules are then transported into an acid mixer(s) to be mixed with acid, wherein concentration and dosage of the acid is based on demands of traditional furfural production process. The corn-cob granules are transported into double hydrolysis reactors in series by belt conveyer after mixed with acid. After the double hydrolysis reactors are full, steam with 1.3-1.6 MPa pressure is introduced, wherein the hydrolysis temperature is from 192° C. to 201° C., and the hydrolysis time is from 0.4 h to 1 h. The raw hydrolyzed furfural liquid is introduced into following processes such as extracting and refining until end product furfural is obtained. The wastewater is disposed according to the method and system of the present invention as shown in FIG. 2. Furfural wastewater is transported into wastewater sediment bowl 1 where solid impurities of furfural wastewater are removed and then transported into the evaporation system, wherein it is firstly pumped into wastewater buffer vessel 4 by wastewater pump 2. The bottom of wastewater buffer vessel 4 is connected with the bottom of wastewater evaporator 3. Hot steam generated in boiler 5 is introduced into wastewater evaporator 3. The furfural wastewater and the hot steam used for heating run in different pipelines inside wastewater evaporator 3, where the furfural wastewater is heated through heat exchange. The wastewater vapor heated from the wastewater in wastewater evaporator 3 containing relative quantities of furfural is transformed into wastewater buffer vessel 4 for being cushioned therein and then is transported back into the hydrolysis reactor through a top wastewater vapor pipeline in order to realize recycle of the furfural wastewater. Since the bottom of wastewater evaporator 3 is connected with the bottom of wastewater buffer vessel 4 via a pipeline(s), the liquid phase generated after the cushion process is drained back from the bottom of wastewater buffer vessel 4 to the bottom of wastewater evaporator 3 to be heated sequentially. In such a way, the heated wastewater is circulated between wastewater buffer vessel 4 and wastewater evaporator 3 continuously.

Titanium alloy is utilized as the part of material of the equipments which is directly contacted with furfural wastewater in the wastewater evaporation system of the present invention. The steam pressure is from 1.6 MPa to 1.9 MPa, while the furfural wastewater vapor pressure is from 1.3 MPa to 1.6 MPa, namely the difference between the two pressures is 0.3 MPa. Condensed water generated after the furfural wastewater is vapored and the residual steam are transported into steam-water separator 6 to generate saturated vapor and condensed water, of which the saturated vapor is provided to steam buffer vessel 7 for a steam user(s), wherein the pressure of steam-water separator 6 and steam buffer vessel 7 is from 1.6 MPa to 1.9 MPa. The condensed water in steam-water separator 6 and steam buffer vessel 7 is transported into steam expansion slot 8 to be depressurized into two parts namely saturated vapor under 0.2-0.5 MPa pressure for a steam user(s) and condensed water to be pumped into a boiler(s) directly. Vapor residues continuously discharged from the bottom of wastewater evaporator 3 containing relative quantities of acetic acid are ejected into coal as combustible fuels. Wastewater containing light components generated during the furfural refining process is transported into the raw furfural liquid distillation column to recover the small quantity of furfural therein, and then the wastewater discharged from the bottom of the raw furfural liquid distillation column is transported into the wastewater disposal system of the present invention. Null-discharge of furfural wastewater is realized within the whole furfural production process. Furfural yield in embodiment 1 is from 9% to 10%. The detailed technical data is shown is Table 1.

Embodiment 2

The raw material utilizes air-dried corn-cobs, which is cleaned and crushed into corn-cob granules in 1-1.5 cm particle size. The corn-cob granules are then transported into an acid mixer(s) to be mixed with acid, wherein concentration and dosage of the acid is based on demands of traditional furfural production process. The corn-cob granules are transported into double hydrolysis reactors in series by belt conveyer after mixed with acid. After the double hydrolysis reactors are full, steam with 1.3-1.6 MPa pressure is introduced, wherein the hydrolysis temperature is from 192° C. to 201° C., and the hydrolysis time is from 0.4 h to 1 h. The raw hydrolyzed furfural liquid is introduced into following processes such as extracting and refining until end product furfural is obtained. The wastewater is disposed according to the method and system of the present invention as shown in FIG. 3. Furfural wastewater is sedimentated to remove the solid impurities and then is transported into wastewater buffer vessel 4 via wastewater pump 2. The bottom of wastewater buffer vessel 4 is connected with the bottom of wastewater evaporator 3. Hot steam generated in boiler 5 is introduced into wastewater evaporator 3. The furfural wastewater and the hot steam used for heating run in different pipelines inside wastewater evaporator 3, where the furfural wastewater is heated through heat exchange. The wastewater vapor heated from the wastewater in wastewater evaporator 3 containing relative quantities of furfural is transmitted into wastewater buffer vessel 4 for being cushioned therein and then is transported back into the hydrolysis reactor through a top wastewater vapor pipeline in order to realize recycle of the furfural wastewater. Since the bottom of wastewater evaporator 3 is connected with the bottom of wastewater buffer vessel 4 via a pipeline(s), the liquid phase generated after the cushion process is drained back from the bottom of wastewater buffer vessel 4 to the bottom of wastewater evaporator 3 to be heated sequentially. In such a way, the heated wastewater is circulated between wastewater buffer vessel 4 and wastewater evaporator 3 continuously.

Titanium alloy is utilized as the part of material of the equipments which is directly contacted with furfural wastewater in the wastewater evaporation system of the present invention. The steam pressure is from 1.6 MPa to 1.9 MPa, while the furfural wastewater vapor pressure is from 1.3 MPa to 1.6 MPa, namely the difference between the two pressures is 0.3 MPa. Condensed water generated after the furfural wastewater is vapored and the residual steam are transported into steam-water separator 6 to generate saturated vapor and condensed water, of which the saturated vapor is provided to steam buffer vessel 7 for a steam user(s), wherein the pressure of steam-water separator 6 and steam buffer vessel 7 is from 1.6-1.9 MPa. The condensed water in steam-water separator 6 and steam buffer vessel 7 is transported into steam expansion slot 8 to be depressurized into two parts namely saturated vapor under 0.2-0.5 MPa pressure for a steam user(s) and condensed water to be pumped into a boiler(s) directly. Vapor residues continuously discharged from the bottom of wastewater evaporator 3 is utilized as diluent solvent of furfural hydrolysis catalyst to be mixed with acid, namely the residues return to original furfural hydrolysis process as diluent solvent of furfural hydrolysis catalyst, which is utilized for mixing with dilute sulfuric acid, and the mixed dilute sulfuric acid is used for soaking raw materials such as corn-cob. This method causes no pollution.

Additionally, the wastewater containing light components generated during the furfural refining process is transported into the raw furfural liquid distillation column to recover the small quantity of furfural therein, and then the wastewater discharged from the bottom of the raw furfural liquid distillation column is transported into the wastewater disposal system of the present invention. Null-discharge of furfural wastewater is realized within the whole furfural production process. The furfural yield in embodiment 2 is from 9% to 10%. The detailed technical data is shown in Table 1.

Embodiment 3

The raw material utilizes air-dried corn-cobs, which is cleaned and crushed into corn-cob granules in 1-1.5 cm particle size. The corn-cob granules are then transported into an acid mixer(s) to be mixed with acid, wherein concentration and dosage of the acid is based on demands of traditional furfural production process. The corn-cob granules are transported into double hydrolysis reactors in series by belt conveyer after mixed with acid. After the double hydrolysis reactors are full, steam with 1.3-1.6 MPa pressure is introduced, wherein the hydrolysis temperature is from 192° C. to 201° C., and the hydrolysis time is from 0.4 h to 1 h. The raw hydrolyzed furfural liquid is introduced into following processes such as extracting and refining until end product furfural is obtained. The wastewater is disposed according to the method and system of the present invention as shown in FIG. 3. Furfural wastewater is sedimentated to remove the solid impurities and then is neutralized by $NaCO_3$. Common austenite stainless steel or carbon steel is utilized as the part of material of the equipments which is directly contacted with furfural wastewater in the wastewater evaporation system of the present invention in order to reduce the cost of equipments to a great extent.

The neutralized furfural wastewater is pumped into wastewater buffer vessel 4 via wastewater pump 2. The bottom of wastewater buffer vessel 4 is connected with the bottom of wastewater evaporator 3. Hot steam generated in boiler 5 is introduced into wastewater evaporator 3. The furfural wastewater and the hot steam used for heating run in different pipelines inside wastewater evaporator 3, where the furfural wastewater is heated through heat exchange. The wastewater vapor heated from the wastewater in wastewater evaporator 3 containing relative quantities of furfural is transmitted into wastewater buffer vessel 4 for being cushioned therein and then is transported back into the hydrolysis reactor through a top wastewater vapor pipeline in order to realize recycle of the furfural wastewater. Since the bottom of wastewater evaporator 3 is connected with the bottom of wastewater buffer vessel 4 via a pipeline(s), the liquid phase generated after the cushion process is drained back from the bottom of wastewater buffer vessel 4 to the bottom of wastewater evaporator 3 to be heated sequentially. In such a way, the heated wastewater is circulated between wastewater buffer vessel 4 and wastewater evaporator 3 continuously.

The steam pressure is from 1.6 MPa to 1.9 MPa, while the furfural wastewater vapor pressure is from 1.3 MPa to 1.6 MPa, namely the difference between the two pressures is 0.3 MPa. Condensed water generated after the furfural wastewater is vapored and the residual steam are transported into steam-water separator 6 to generate saturated vapor and condensed water, of which the saturated vapor is provided to steam buffer vessel 7 for a steam user(s), wherein the pressure of steam-water separator 6 and steam buffer vessel 7 is from 1.6-1.9 MPa. The condensed water in steam-water separator 6 and steam buffer vessel 7 is transported into steam expansion slot 8 to be depressurized into two parts namely saturated vapor under 0.2-0.5 MPa pressure for a steam user(s) and condensed water to be pumped into a boiler(s) directly. Vapor residues are continuously discharged from the bottom of wastewater evaporator 3. The wastewater containing light components generated during the furfural refining process is transported into the raw furfural liquid distillation column to recover the small quantity of furfural therein, and then the wastewater discharged from the bottom of the raw furfural liquid distillation column is transported into the wastewater disposal system of the present invention. Null-discharge of furfural wastewater is realized within the whole furfural production process. The vapor residues are made into by-product—sodium acetate after processes such as filtration, discoloration, evaporation/condensation, crystallization and etc. No wastewater is generated during this process. Other compounds such as NaOH or $Ca(OH)_2$ can also be utilized as the neutralizer. The furfural yield in embodiment 3 is from 9% to 10%. The detailed technical data is shown in Table 1.

Embodiment 4

The raw material utilizes air-dried corn-cobs, which is cleaned and crushed into corn-cob granules 1-1.5 cm particle size. The corn-cob granules are then transported into an acid mixer(s) to be mixed with acid, wherein concentration and dosage of the acid is based on demands of traditional furfural production process. The corn-cob granules are transported into double hydrolysis reactors in series by belt conveyer after mixed with acid. After the double hydrolysis reactors are full, steam with 1.3-1.6 MPa pressure is introduced, wherein the hydrolysis temperature is from 192° C. to 201° C., and the hydrolysis time is from 0.4 h to 1 h. The raw hydrolyzed furfural liquid is introduced into following processes such as extracting and refining until end product furfural is obtained. The wastewater is disposed according to the method and system of the present invention as shown in FIG. 4. Furfural wastewater is sedimentated to remove the solid impurities and then is transported into wastewater buffer vessel 4 via wastewater pump 2. The bottom of wastewater buffer vessel 4 is connected with the bottom of wastewater evaporator 3. The wastewater is heated and vapored by an electric heating furnace(s) with 380V voltage according to this embodiment. Titanium alloy is utilized as the part of material of the equipments which is directly contacted with furfural wastewater in the wastewater evaporation system of the present invention. The wastewater vapor heated from the wastewater in wastewater evaporator 3 containing relative quantities of furfural is transmitted into wastewater buffer vessel 4 for being cushioned therein and then is transported back into the hydrolysis reactor through a top wastewater vapor pipeline in order to realize recycle of the furfural wastewater. Since the bottom of wastewater evaporator 3 is connected with the bottom of wastewater buffer vessel 4 via a pipeline(s), the liquid phase generated after the cushion process is drained back from the bottom of wastewater buffer vessel 4 to the bottom of wastewater evaporator 3 to be heated sequentially. In such a way, the heated wastewater is circulated between wastewater buffer vessel 4 and wastewater evaporator 3 continuously.

Pressure of the furfural wastewater vapor is from 1.3 MPa to 1.6 MPa, and vapor residues continuously discharged from the bottom of wastewater evaporator 3 are mixed with acid as diluent solvent of furfural hydrolysis catalyst. The wastewater containing light components generated during the furfural refining process are also transported into the raw furfural liquid distillation column to recover the small quantity of furfural therein. Wastewater is transported circularly into the wastewater disposal system of the present invention. Null-discharge of the furfural wastewater is realized during the whole production process. Furfural yield of embodiment 4 is from 9 to 10%. The detailed technical data is shown in Table 1.

Embodiment 5

The raw material utilizes air-dried corn-cobs, which is cleaned and crushed into corn-cob granules in 1-1.5 cm particle size. The corn-cob granules are then transported into an acid mixer(s) to be mixed with acid, wherein concentration and dosage of the acid is based on demands of traditional furfural production process. The corn-cob granules are transported into double hydrolysis reactors in series by belt conveyer after mixed with acid. After the double hydrolysis reactors are full, steam with 1.3-1.6 MPa pressure is introduced, wherein the hydrolysis temperature is from 192° C. to 201° C., and the hydrolysis time is from 0.4 h to 1 h. The raw hydrolyzed furfural liquid is introduced into following processes such as extracting and refining until end product furfural is obtained. The wastewater is disposed according to the method and system of the present invention as shown in FIG. 5. Furfural wastewater is sedimentated to remove the solid impurities and then is transported into wastewater buffer vessel 4 via wastewater pump 2. The bottom of wastewater buffer vessel 4 is connected with the bottom of wastewater evaporator 3.

The wastewater is heated and vapored by a coal heating furnace(s) in this embodiment, which will not be explained in details since it is not the key issue of the present invention. Titanium alloy is utilized as the part of material of the equipments which is directly contacted with furfural wastewater in the wastewater evaporation system of the present invention. The wastewater vapor heated from the wastewater in wastewater evaporator 3 containing relative quantities of furfural is transmitted into wastewater buffer vessel 4 for being cushioned therein and then is transported back into the hydrolysis reactor through a top wastewater vapor pipeline in order to realize recycle of the furfural wastewater. Since the bottom of wastewater evaporator 3 is connected with the bottom of wastewater buffer vessel 4 via a pipeline(s), the liquid phase generated after the cushion process is drained back from the bottom of wastewater buffer vessel 4 to the bottom of wastewater evaporator 3 to be heated sequentially. In such a way, the heated wastewater is circulated between wastewater buffer vessel 4 and wastewater evaporator 3 continuously.

Pressure of the furfural wastewater vapor is from 1.3 MPa to 1.6 MPa, and vapor residues continuously discharged from the bottom of wastewater evaporator 3 are mixed with acid as diluent solvent of furfural hydrolysis catalyst. The wastewater containing light components generated during the furfural refining process are also transported into the raw furfural liquid distillation column to recover the small quantity of furfural therein. Wastewater is transported circularly into the wastewater disposal system of the present invention. Null-discharge of the furfural wastewater is realized during the whole production process. Furfural yield of embodiment 5 is from 9 to 10%. The detailed technical data is shown in Table 1.

Embodiment 6

The raw material utilizes air-dried corn-cobs, which is cleaned and crushed into corn-cob granules in 1-1.5 cm particle size. The corn-cob granules are then transported into an acid mixer(s) to be mixed with acid, wherein concentration and dosage of the acid is based on demands of traditional furfural production process. The corn-cob granules are transported into double hydrolysis reactors in series by belt conveyer after mixed with acid. After the double hydrolysis reactors are full, steam with 1.3-1.6 MPa pressure is introduced, wherein the hydrolysis temperature is from 192° C. to 201° C., and the hydrolysis time is from 0.4 h to 1 h. The raw hydrolyzed furfural liquid is introduced into following processes such as extracting and refining until end product furfural is obtained. The wastewater is disposed according to the method and system of the present invention as shown in FIG. 5. Furfural wastewater is sedimentated to remove the solid impurities and then is transported into wastewater buffer vessel 4 via wastewater pump 2. The bottom of wastewater buffer vessel 4 is connected with the bottom of wastewater evaporator 3.

The wastewater is heated and vapored by an oil/gas heating furnace(s) in this embodiment, which will not be explained in details since it is not the key issue of the present invention. Titanium alloy is utilized as the part of material of the equipments which is directly contacted with furfural wastewater in the wastewater evaporation system of the present invention. The wastewater vapor heated from the wastewater in wastewater evaporator 3 containing relative quantities of furfural is transmitted into wastewater buffer vessel 4 for being cushioned therein and then is transported back into the hydrolysis reactor through a top wastewater vapor pipeline in order to realize recycle of the furfural wastewater. Since the bottom of wastewater evaporator 3 is connected with the bottom of wastewater buffer vessel 4 via a pipeline(s), the liquid phase generated after the cushion process is drained back from the bottom of wastewater buffer vessel 4 to the bottom of wastewater evaporator 3 to be heated sequentially. In such a way, the heated wastewater is circulated between wastewater buffer vessel 4 and wastewater evaporator 3 continuously.

Pressure of the furfural wastewater vapor is from 1.3 MPa to 1.6 MPa, and vapor residues continuously discharged from the bottom of wastewater evaporator 3 are mixed with acid as diluent solvent of furfural hydrolysis catalyst. The wastewater containing light components generated during the furfural refining process are also transported into the raw furfural liquid distillation column to recover the small quantity of furfural therein. Wastewater is transported circularly into the wastewater disposal system of the present invention. Null-discharge of the furfural wastewater is realized during the whole production process. Furfural yield of embodiment 6 is from 9 to 10%. The detailed technical data is shown in Table 1.

It has been already disclosed according to the above embodiments that the method and system for the disposal of furfural wastewater of the present invention realize null-discharge of pollutants due to no wastewater is discharged, and even just the small quantities of residues is utilized harmlessly. Meanwhile, neither the yield nor the quality of the furfural products is negatively affected.

TABLE 1

| technical data name | requirement according to GB 1926.1-88 for high-grade products | traditional embodiment | embodiment 1 | embodiment 2 | embodiment 3 | embodiment 4 | embodiment 5 | embodiment 6 |
|---|---|---|---|---|---|---|---|---|
| density, $\rho_{20}$ g/cm$^3$ | 1.159-1.161 | 1.161 | 1.161 | 1.160 | 1.161 | 1.161 | 1.159 | 1.160 |
| refraction, ($n_D^{20}$) | 1.524-1.527 | 1.524 | 1.525 | 1.525 | 1.526 | 1.527 | 1.527 | 1.525 |
| moisture content, % ≤ | 0.05 | 0.031 | 0.035 | 0.029 | 0.038 | 0.037 | 0.036 | 0.027 |
| acidity, mol/l ≤ | 0.008 | 0.0026 | 0.0024 | 0.0025 | 0.0027 | 0.005 | 0.0036 | 0.0045 |
| furfural content, % ≥ | 99.0 | 99.08 | 99.12 | 99.05 | 99.10 | 99.02 | 99.17 | 99.15 |
| initial boiling point, ° C. | 155 | 158.4 | 158.6 | 158.0 | 158.1 | 157.8 | 157.6 | 156.6 |
| fraction before 158 ° C., ml ≤ | 2 | 0 | 0 | 0 | 0 | 0 | 0 | 0 |
| total distillation quantity, % ≥ | 99.0 | 99.3 | 99.2 | 99.1 | 99.2 | 99.4 | 99.3 | 99.1 |
| final distillation point, ° C. ≤ | 170 | 169.2 | 169.6 | 169.1 | 169.3 | 169.6 | 169.5 | 169.4 |
| residues, % ≤ | 1.0 | 0.40 | 0.39 | 0.31 | 0.34 | 0.54 | 0.47 | 0.45 |

From the above table, it can be seen that all of the embodiments of the present invention have reached or exceeded the relating requirements according to China's national standards GB 1926.1-88. Meanwhile compared with the embodiment of traditional technology, the present invention realizes null-discharge of furfural wastewater. Even the small quantities of residues thereof have been utilized effectively.

It is also understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method for disposal of furfural wastewater, comprising:
   Treating raw crop material by crushing and mixing with acid and hydrolyzing in a hydrolysis reactor to form raw furfural liquid;
   transporting, said raw furfural liquid is transported to a distillation column to obtain furfural wastewater, then transporting said furfural wastewater to wastewater evaporation system;
   Heating the furfural wastewater to form wastewater vapor; and
   recycling said wastewater vapor to said hydrolysis reactor to form a recycle of said furfural wastewater; and
   Recycling vapor residue from the wastewater evaporation system wherein the wastewater vapor residue provides the acetic acid for hydrolyzing the raw crop material.

2. The method according to claim 1 further comprising separating furfural sediment from said furfural wastewater after it is discharged from said distillation column.

3. The method according to claim 1 further comprising generating wastewater vapor residues comprising acetate.

4. The method according to claim 3 wherein said heating utilizes steam, electricity, coal, oil, gas, plant straws or said wastewater vapor residues.

5. The method according to claim 1 wherein said heating utilizes steam, wherein after heat exchange with said furfural wastewater, said steam is separated into separated steam and separated condensed water, wherein said separated steam is supplied to a steam user(s), said separated condensed water is depressurized and expanded into low pressure steam which is supplied to a steam user(s) and superheated condensed water is directly pumped into a boiler(s) by a water pump so as to realize recycle of soft water.

6. The method according to claim 3 wherein pressure of said wastewater vapor has a vapor pressure that is higher than reaction pressure of said hydrolysis reactor, and pressure difference between the two ranges from 0.01 MPa to 1 MPa.

7. The method according to claim 5 wherein pressure of said steam is higher than pressure of said wastewater vapor, and pressure difference between the two ranges from 0.01 MPa to 1 MPa.

8. A system for disposal of furfural wastewater comprising:
   a hydrolysis reactor for treating raw crop material which is crushed and mixed with acid, a distillation column, connecting with said hydrolysis reactor, said distillation column discharging said furfural wastewater, characterized in that,
   said system for disposal of furfural wastewater comprises a wastewater evaporation system, for heating said furfural wastewater discharged from said distillation column and generating wastewater vapor, and said wastewater evaporation system connecting with said hydrolysis reactor by a wastewater vapor pipeline(s).

9. The system according to claim 8 further comprising a wastewater buffer vessel connecting with said wastewater evaporation system, said furfural wastewater being transported into said wastewater evaporation system via said wastewater buffer vessel which is equipped with a regulator for regulating the balance between said wastewater vapor generated from said wastewater evaporation system and the inputting wastewater thereinto.

10. The system according to claim 8 wherein said wastewater evaporation system at least comprises a wastewater evaporator, connecting with a heat resource.

11. The system according to claim 9 wherein said wastewater evaporation system comprises a wastewater evaporator, connecting with said wastewater buffer vessel.

12. The system according to claim 8 wherein said distillation column is connecting with at least one wastewater sediment bowl thereafter.

13. The system according to claim 8 wherein said wastewater evaporation system comprises outlet for discharging wastewater vapor residues.

14. The system according to claim 10 wherein said heat resource comprises a vapor heating system which comprises:
   a boiler, connecting with said wastewater evaporator, for generating steam used for heating which is transported into said wastewater evaporator, said furfural wastewater and said steam used for heating run respectively via different pipelines inside said wastewater evaporator and said furfural wastewater is heated by means of heat exchange;
   a steam-water separator, connecting with said wastewater evaporator, wherein said steam used for heating after heat exchange in said wastewater evaporator is transported into said steam-water separator to be separated into steam and condensed water;
   a steam buffer vessel, connecting with said steam-water separator, said steam generated in said steam-water separator is transported into said steam buffer vessel to be cushioned and then supplied to a steam user(s);
   a steam expansion slot, connecting with said steam-water separator and said steam buffer vessel, wherein the condensed water generated in both said steam-water separator and said steam buffer vessel is transported into said steam expansion slot to be depressurized and expended for generating low pressure steam which is supplied to a steam user(s), and also for generating condensed water which is directly transported into said boiler to realize recycle of soft water.

15. The system according to claim 10 wherein said heat resource is any one or any combination on utilization of electricity, coal, oil, gas, plant straws or said wastewater vapor residues.

16. A method for furfural production, comprising:
   Crushing a raw crop material and mixing the crushed raw crop material with dilute sulfuric acid;
   transporting the raw crop material into a hydrolysis reactor to form raw furfural liquid,
   transporting said raw furfural liquid into a distillation column to be distilled, the raw furfural liquid being an azeotrope of furfural and water
   distilling the azeotrope out from the top of said distillation column and transforming into raw furfural after cooling,
   transporting the raw furfural into a refining system to be refined into end product furfural,
   discharging furfural wastewater from bottom of said distillation column, and disposing of furfural wastewater.

17. The method according to claim 16 wherein the wastewater vapor residues formed after said furfural wastewater is heated into wastewater vapor are harmlessly disposed via one of three methods as follows:
   (1) utilized as fuels of boiler directly;
   (2) utilized as hydrolysis mixed acid in furfural production in the form of concentrated liquid;
   (3) said furfural wastewater is neutralized with adding alkali compounds before step (a) in order to generate vapor residues including acetate solution.

* * * * *